(12) United States Patent
Nesvadba et al.

(10) Patent No.: US 9,255,217 B2
(45) Date of Patent: Feb. 9, 2016

(54) IMINOXYTRIAZINES AS RADICAL GENERATORS

(71) Applicant: BASF SE, Ludwigshafen (DE)

(72) Inventors: Peter Nesvadba, Marly (CH); Lucienne Bugnon Folger, Pfeffingen (CH); Antoine Carroy, Limburgerhof (DE); Marc Faller, Hegenheim (FR)

(73) Assignee: BASF SE (DE)

( * ) Notice: Subject to any disclaimer, the term of this patent is extended or adjusted under 35 U.S.C. 154(b) by 0 days.

(21) Appl. No.: 14/437,246

(22) PCT Filed: Oct. 22, 2013

(86) PCT No.: PCT/EP2013/072006
§ 371 (c)(1),
(2) Date: Apr. 21, 2015

(87) PCT Pub. No.: WO2014/064064
PCT Pub. Date: May 1, 2014

(65) Prior Publication Data
US 2015/0284604 A1    Oct. 8, 2015

Related U.S. Application Data

(60) Provisional application No. 61/717,127, filed on Oct. 23, 2012.

(30) Foreign Application Priority Data

Oct. 23, 2012  (EP) ................................ 12189566

(51) Int. Cl.
| | |
|---|---|
| C07D 251/30 | (2006.01) |
| C07D 251/42 | (2006.01) |
| C07D 403/14 | (2006.01) |
| C09J 133/14 | (2006.01) |
| C09D 11/107 | (2014.01) |

(52) U.S. Cl.
CPC ............. *C09J 133/14* (2013.01); *C09D 11/107* (2013.01)

(58) Field of Classification Search
CPC .............................. C09J 133/14; C09D 11/107
See application file for complete search history.

(56) References Cited

U.S. PATENT DOCUMENTS 3,844,916 A   10/1974  Gaske
4,619,956 A   10/1986  Susi (Continued)

FOREIGN PATENT DOCUMENTS

EP        280222 A2    8/1988
EP        0434608 A1   6/1991

(Continued)

OTHER PUBLICATIONS

International Search Report for PCT/EP2013/072006 mailed Nov. 21, 2013.
Y. Furuya et al., "Cyanuric Chloride as a Mild and Active Beckmann Rearrangement Catalyst", J. Am. Chem. Soc., vol. 127, No. 32, pp. 11240-11241, 2005.

(Continued)

*Primary Examiner* — Robert Harlan
(74) *Attorney, Agent, or Firm* — Drinker Biddle & Reath LLP

(57) ABSTRACT

Iminoxytriazine compounds of the formula I

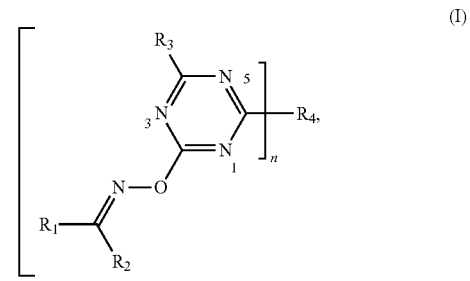

wherein
n is 1 or 2;
$R_1$ and $R_2$ independently of each other are hydrogen, $NH_2$, $NHR_5$, $NR_5R_6$, $COR_5$, $COOR_5$, $CONH_2$, $CONHR_5$, $CONR_5R_6$, $CN$, $SR_5$, $OR_5$, $C_1$-$C_{18}$alkyl, $C_3$-$C_{12}$cycloalkyl, $C_6$-$C_{14}$aryl or $C_2$-$C_{14}$heteroaryl, wherein said $C_3$-$C_{12}$cycloalkyl, $C_6$-$C_{14}$aryl or $C_2$-$C_{14}$heteroaryl is unsubstituted or substituted by one or more radicals selected from the group consisting of $C_1$-$C_{12}$alkyl, $C_3$-$C_{12}$-cycloalkyl, phenyl, halogen and $C_1$-$C_{12}$ alkoxy,
or $R_1$ and $R_2$ together with the C atom to which they are linked form a 4 to 12 membered carbocyclic or heterocyclic saturated or unsaturated ring which is unsubstituted or substituted by one or more radicals selected from the group consisting of $C_1$-$C_{12}$alkyl, $C_3$-$C_{12}$-cycloalkyl, phenyl, halogen and $C_1$-$C_{12}$ alkoxy;
$R_3$ is F, Cl, OH, $OR_5$, SH, $SR_5$, $NH_2$, $NHR_5$, $NR_5R_6$ or $R_1R_2C{=}N{-}O{-}$;
wherein $R_1$ and $R_2$ in all groups $R_1R_2C{=}N{-}O{-}$ in the compound of the formula I are identical or different;
if n is 1, $R_4$ is F, Cl, OH, $OR_5$, SH, $SR_5$, $NH_2$, $NHR_5$, $NR_5R_6$ or $R_1R_2C{=}N{-}O{-}$;
wherein $R_1$ and $R_2$ in all groups $R_1R_2C{=}N{-}O{-}$ in the compound of the formula I are identical or different;
if n is 2, $R_4$ is a difunctional group derived from a diol, diamine, aminoalcohol or mercaptoalcohol;
$R_5$ and $R_6$ independently of each other are $C_1$-$C_{18}$alkyl, $C_3$-$C_{12}$cycloalkyl, $C_6$-$C_{14}$aryl or $C_2$-$C_{14}$heteroaryl; are suitable as radical generating agents.

11 Claims, No Drawings

(56) References Cited

U.S. PATENT DOCUMENTS

| | | |
|---|---|---|
| 5,198,498 A | 3/1993 | Valet et al. |
| 5,298,067 A | 3/1994 | Valet et al. |
| 5,322,868 A | 6/1994 | Valet et al. |
| 5,369,140 A | 11/1994 | Valet et al. |
| 5,482,649 A | 1/1996 | Meixner et al. |
| 5,734,002 A | 3/1998 | Reich et al. |

FOREIGN PATENT DOCUMENTS

| | | | |
|---|---|---|---|
| EP | 0704437 A2 | | 4/1996 |
| EP | 2 241 552 A1 | * | 10/2010 |
| EP | 2241552 A1 | | 10/2010 |
| GB | 229709 A | | 8/1925 |
| JP | 2009271502 A | | 11/2009 |
| WO | WO 94/18278 | * | 8/1994 |
| WO | WO-94/18278 A2 | | 8/1994 |
| WO | WO-96/28431 A1 | | 9/1996 |
| WO | WO-01/90113 A1 | | 11/2001 |
| WO | WO-2004/081100 A1 | | 9/2004 |
| WO | WO-2006/051047 A1 | | 5/2006 |
| WO | WO-2010/079102 A1 | | 7/2010 |
| WO | WO 2010/112410 A1 | * | 10/2010 |
| WO | WO-2010/112410 A1 | | 10/2010 |
| WO | WO-2010128062 A1 | | 11/2010 |

* cited by examiner

IMINOXYTRIAZINES AS RADICAL GENERATORS

CROSS-REFERENCE TO RELATED APPLICATIONS

This application is a national stage application (under 35 U.S.C. §371) of PCT/EP2013/072006, filed Oct. 22, 2013, which claims benefit of European Application No. 12189566.8, filed Oct. 23, 2012, and U.S. Application No. 61/717,127, filed Oct. 23, 2012, all of which are incorporated herein by reference in their entirety.

The invention relates to the use of iminoxytriazine compounds as source of radicals (in particular as polymerization initiators), to polymerizable compositions comprising these iminoxytriazines and to new iminoxytriazine compounds.

Radical polymerization belongs to the most important polymerization methods. It is used for preparing many commercially important polymers such as polystyrene, PVC, polyacrylates, polymethacrylates, PAN and other polymers. For technical details, reference may be made to the standard work G. Odian, Principles of Polymerization, McGraw-Hill New York 1991.

Radical polymerizations are started using initiators. Examples of initiators which have become established in polymer technology are azo compounds, dialkyl peroxides, diacyl peroxides, hydroperoxides, thermolabile C—C-dimers, redox systems and photoinitiators. Reference is made to the "Handbook of Free Radical Initiators", (E T. Denisov, T. G. Denisova, T. S. Pokidova, J. Wiley & Sons, Inc. Hoboken, New Jersey, 2003).

Despite their widespread use, the known polymerization initiators have various disadvantages. Thus, for example, peroxides are extremely readily ignitable and sustain fire and present thus potential explosion hazards, so that their manufacture, storage, transport and use has to involve costly safety precautions. Some initiators further generate toxic products, as e.g. AIBN.

There is therefore a general need for new initiators for radical polymerization processes which have a satisfactory safety profile.

WO2001/90113 and WO2004/081100/A1, describe sterically hindered N-acyloxyamines as a new class of polymerization initiators.

Further new polymerization initiators are N-substituted imides as described in WO2006/051047, O-dialkylamino-isoureas reported in WO2010/079102, O-iminoisoures reported in WO2010/128062 and aryltriazenes reported in WO2010/112410.

It has now been found that iminoxy-triazines are very efficient initiators of radical polymerization or of other processes which are triggered off by radicals, for example the controlled degradation of polyolefins.

Subject of the invention accordingly is a composition comprising (a) an ethylenically unsaturated, polymerizable monomer or oligomer and (b) as radical generating compound an iminoxytriazine compound of the formula I

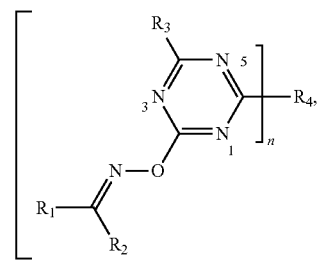

wherein
n is 1 or 2;
$R_1$ and $R_2$ independently of each other are hydrogen, $NH_2$, $NHR_5$, $NR_5R_6$, $COR_5$, $COOR_5$, $CONH_2$, $CONHR_5$, $CONR_5R_6$, CN, $SR_5$, $OR_5$, $C_1$-$C_{18}$alkyl, $C_3$-$C_{12}$cycloalkyl, $C_6$-$C_{14}$aryl or $C_2$-$C_{14}$heteroaryl,
wherein said $C_3$-$C_{12}$cycloalkyl, $C_6$-$C_{14}$aryl or $C_2$-$C_{14}$heteroaryl is unsubstituted or substituted by one or more radicals selected from the group consisting of $C_1$-$C_{12}$alkyl, $C_3$-$C_{12}$-cycloalkyl, phenyl, halogen and $C_1$-$C_{12}$ alkoxy,
or $R_1$ and $R_2$ together with the C atom to which they are linked form a 4 to 12 membered carbocyclic or heterocyclic saturated or unsaturated ring which is unsubstituted or substituted by one or more radicals selected from the group consisting of $C_1$-$C_{12}$alkyl, $C_3$-$C_{12}$-cycloalkyl, phenyl, halogen and $C_1$-$C_{12}$ alkoxy;
$R_3$ is F, Cl, OH, $OR_5$, SH, $SR_5$, $NH_2$, $NHR_5$, $NR_5R_6$ or $R_1R_2C$=N—O—;
wherein $R_1$ and $R_2$ in all groups $R_1R_2C$=N—O— in the compound of the formula I are identical or different;
if n is 1, $R_4$ is F, Cl, OH, $OR_5$, SH, $SR_5$, $NH_2$, $NHR_5$, $NR_5R_6$ or $R_1R_2C$=N—O—;
wherein $R_1$ and $R_2$ in all groups $R_1R_2C$=N—O— in the compound of the formula I are identical or different;
if n is 2, $R_4$ is a difunctional group derived from a diol, diamine, aminoalcohol or mercaptoalcohol;
$R_5$ and $R_6$ independently of each other are $C_1$-$C_{18}$alkyl, $C_3$-$C_{12}$cycloalkyl, $C_6$-$C_{14}$aryl or $C_2$-$C_{14}$heteroaryl.

The compounds of the formula I are very efficient initiators of radical polymerizations or radical curing. This is their preferred application.

However, the use of the inventive compounds is not limited to polymerizations or curing processes. Rather, the inventive iminoxytriazines can be used in other processes which are triggered off by radicals, for example in controlled degradation of polyolefines, for crosslinking of polymers such as polyethylene or unsaturated rubber, or as initiators for chemical reactions which proceed via radical mechanism. Such reactions are well known in chemistry and extensively described in standard works (e.g. Radicals in Organic Synthesis, P. Renaud & M. P. Sibi (Editors), Wiley-VCH, 2001 or Encyclopedia of Radicals in Chemistry, Biology and Materials, John Wiley & Sons, Ltd., 2012).

The generation of radicals from the iminoxytriazines and the processes triggered by these radicals can be effected by different stimuli, preferably by heat but also by electromagnetic radiation such as X-ray, ultraviolet, visible or infrared light or by actinic radiation such as for example γ-radiation (electron beam).

Furthermore, most of these Iminoxytriazines are novel compounds.

Subject of the invention therefore also are iminoxytriazine compounds of the formula I as shown above, wherein $R_1$ and $R_2$ independently of each other are hydrogen, $NH_2$, $NHR_5$, $NR_5R_6$, $COR_5$, $COOR_5$, $CONH_2$, $CONHR_5$, $CONR_5R_6$, CN, $SR_5$, $OR_5$, $C_1$-$C_{18}$alkyl, $C_3$-$C_{12}$cycloalkyl, $C_6$-$C_{14}$aryl or $C_2$-$C_{14}$heteroaryl, wherein said $C_3$-$C_{12}$cycloalkyl, $C_6$-$C_{14}$aryl or $C_2$-$C_{14}$heteroaryl is unsubstituted or substituted by one or more radicals selected from the group consisting of $C_1$-$C_{12}$alkyl, $C_3$-$C_{12}$-cycloalkyl, phenyl, halogen and $C_1$-$C_{12}$ alkoxy, or $R_1$ and $R_2$ together with the C atom to which they are linked form a 4 to 12 membered carbocyclic or heterocyclic saturated or unsaturated ring which is unsubstituted or substituted by one or more radicals selected from the group consisting of $C_1$-$C_{12}$alkyl, $C_3$-$C_{12}$-cycloalkyl, phenyl, halogen and $C_1$-$C_{12}$ alkoxy;

$R_3$ is $R_1R_2C$=N—O—;

if n is 1, $R_4$ is F, Cl, OH, $OR_5$, SH, $SR_5$, $NH_2$, $NHR_5$, $NR_5R_6$ or $R_1R_2C$=N—O—;

wherein $R_1$ and $R_2$ in all groups $R_1R_2C$=N—O— in the compound of the formula I are identical or different;

if n is 2, $R_4$ is a difunctional group derived from a diol, diamine, aminoalcohol or mercaptoalcohol;

$R_5$ and $R_6$ independently of each other are $C_1$-$C_{18}$alkyl, $C_3$-$C_{12}$cycloalkyl, $C_6$-$C_{14}$aryl or $C_2$-$C_{14}$heteroaryl;

provided that
(i) if $R_4$ is $R_1R_2C$=N—O—, $R_1$ and $R_2$ together with the C atom to which they are linked do not form unsubstituted cyclohexyl or unsubstituted cyclododecyl;
(ii) if $R_4$ is $R_1R_2C$=N—O—, $R_1$ and $R_2$ are not both methyl;
(iii) if $R_4$ is $R_1R_2C$=N—O—, and $R_1$ is methyl, $R_2$ is not phenyl;
(iv) if $R_1$ and $R_2$ are both methyl, or if $R_1$ and $R_2$ together with the C atom to which they are linked form unsubstituted cyclohexyl or unsubstituted cyclododecyl, $R_4$ is not Cl;
(v) if $R_1$ and $R_2$ are both methyl and $R_4$ is $OR_5$, $R_5$ is not 4-methyl-coumarin-7-yl.

$C_1$-$C_{18}$alkyl is linear or branched and is, for example, $C_1$-$C_{14}$-, $C_1$-$C_{12}$-, $C_1$-$C_8$-, $C_1$-$C_6$- or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl and octadecyl.

$C_3$-$C_{12}$cycloalkyl is a mono- or polycyclic aliphatic ring, for example a mono-, bi- or tricyclic aliphatic ring, e.g. $C_5$-$C_{12}$-, $C_5$-$C_{10}$-, $C_3$-$C_{10}$cycloalkyl. Examples of monocyclic rings are cyclopropyl, cyclobutyl, cyclopentyl, cyclohexyl, or cycloheptyl, especially cyclopentyl and cyclohexyl. Examples of polycyclic rings are perhydronaphthyl, adamantyl, bicyclo[1.1.1]pentyl, bicyclo[4.2.2]decyl, bicyclo[2.2.2] octyl, bicyclo[3.3.2]decyl, bicyclo[4.3.2]undecyl, bicyclo [4.3.3]dodecyl, bicyclo[3.3.3]undecyl, bicyclo[4.3.1]decyl, bicyclo[4.2.1]nonyl, bicyclo[3.3.1]nonyl, bicyclo[3.2.1]octyl,

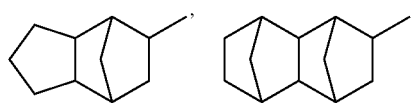

and the like. Also "spiro"-cycloalkyl compounds are covered by the definition $C_3$-$C_{12}$cycloalkyl in the present context, e.g. spiro[5.2]octyl, spiro[5.4]decyl, spiro[5.5]undecyl.

$C_6$-$C_{14}$aryl is for example phenyl, naphthyl, anthryl or phenanthryl, in particular phenyl or naphthyl, preferably phenyl.

$C_2$-$C_{14}$heteroaryl is meant to comprise either one ring or a multiple ring system, e.g. a fused ring-system. Heteroatoms for example are O, S, N. Examples of $C_2$-$C_{14}$heteroaryl are thienyl, benzo[b]thienyl, naphtho[2,3-b]thienyl, thianthrenyl, furyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl or phenanthryl. $C_3$-$C_{20}$heteroaryl in particular is thienyl, furyl, imidazolyl, benzo[b]thienyl, thianthrenyl, thioxanthyl, 1-methyl-2-indolyl or 1-methyl-3-indolyl.

Substituted $C_3$-$C_{12}$cycloalkyl, $C_6$-$C_{14}$aryl or $C_2$-$C_{14}$heteroaryl are substituted by one or more substituents, e.g. 1-6, 1-5, 1-4, 1-3 or one or two substituents. Substituents on the phenyl ring are preferably in positions 2 or in 2, 6 or 2, 4, 6 configuration on the phenyl ring.

Examples for 4 to 12 membered carbocyclic or heterocyclic rings which are formed by $R_1$ and $R_2$ together with the C atom to which they are linked are cyclopropyl, cyclobutyl, cyclopentyl, cyclohexyl, cycloheptyl, tetrahydrofuranyl, tetrahydropyranyl, pyrrolidinyl, e.g. pyrrolidin-2-yl, piperidinyl, piperazinyl, 1,3-diazolidin-2-yl; especially cyclopentyl, cyclohexyl, pyrrolidin-2-yl, 1,3-diazolidin-2-yl, in particular pyrrolidin-2-yl, 1,3-diazolidin-2-yl.

Examples of difunctional groups derived from a diol, diamine, aminoalcohol or mercaptoalcohol for $R_4$, if n is 2, are —O—$(CH_2)_{2\text{-}12}$O—, —NH—$(CH_2)_{2\text{-}12}$NH—, —O—$(CH_2)_{2\text{-}12}$NH—, —S—$(CH_2)_2$—O—, —O—$C_6H_4$O—, —O—$C_6H_4$NH—, —NH—$C_6H_4$NH—, etc.

It is clear that the examples given above are intended to be non-limiting and just for illustration of the definitions.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated above for the compounds according to the present invention in the context of this invention are intended to refer to all categories of the claims, that is to the compositions, use, process claims as well.

It is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "about" as used in connection with a numerical value throughout the description and the claims denotes an interval of accuracy, familiar and acceptable to a person skilled in the art. Said interval is +/−10%.

Preferred are compositions as described above, wherein the compound of the formula I, $R_1$ and $R_2$ independently of each other are hydrogen, $NH_2$, $COR_5$, $C_1$-$C_{12}$alkyl or phenyl, or $R_1$ and $R_2$ together with the C atom to which they are linked form a 6 or 12 membered saturated carbocyclic ring or a 5 membered saturated heterocyclic ring which is substituted by one or more radicals selected from the group consisting of $C_1$-$C_{12}$alkyl and $C_3$-$C_{12}$-cycloalkyl;

$R_3$ and $R_4$ are $R_1R_2C{=}N{-}O{-}$;

wherein $R_1$ and $R_2$ in all groups $R_1R_2C{=}N{-}O{-}$ in the compound of the formula I are identical or different; and $R_5$ is $C_1$-$C_{12}$alkyl.

Emphasis has to be laid on iminoxytriazine compounds of the formula I, as described above, wherein $R_4$ is $R_1R_2C{=}N{-}O{-}$;

wherein $R_1$ and $R_2$ in all groups $R_1R_2C{=}N{-}O{-}$ in the compound of the formula IA are identical or different;

provided that (i) if $R_4$ is $R_1R_2C{=}N{-}O{-}$, $R_1$ and $R_2$ together with the C atom to which they are linked do not form unsubstituted cyclohexyl or unsubstituted cyclododecyl;

(ii) if $R_4$ is $R_1R_2C{=}N{-}O{-}$, $R_1$ and $R_2$ are not both methyl;

(iii) if $R_4$ is $R_1R_2C{=}N{-}O{-}$, and $R_1$ is methyl, $R_2$ is not phenyl.

In particular interesting are compounds of the formula I, wherein $R_3$ and $R_4$ both are $R_1R_2C{=}N{-}O{-}$, and wherein $R_1$ and $R_2$ in all groups $R_1R_2C{=}N{-}O{-}$ in the compound of the formula I are identical or different.

The compounds according to the invention are readily prepared by reaction of oxime derivatives with halogen derivatives of 1,3,5-triazine.

The compounds bearing 3 iminoxy groups are for example readily made by reaction of 2,4,6-trichloro-1,3,5-triazine (cyanuric chloride) with the corresponding oximes. The more reactive cyanuric fluoride can be used instead of cyanuric chloride, while the reaction also can be conducted using cyanuric bromide or iodide. It is well known that the chlorine atoms of cyanuric chloride can be replaced by different nucleophiles in a stepwise manner under increasingly forcing conditions, typically at progressively increasing temperature [see Blotny, Grzegorz, Tetrahedron (2006), 62(41), 9507-9522]. Consequently, if three different oximes are used, that is first $R_1R_2C{=}NOH$ followed by $R'_1R'_2C{=}NOH$ and then $R''_1R''_2C{=}NOH$, iminoxytriazines bearing 3 different iminoxy groups can be made. On the other hand, substitution of all halogen atoms with the same oxime $R_1R_2C{=}NOH$ affords the symmetrical iminoxytriazines.

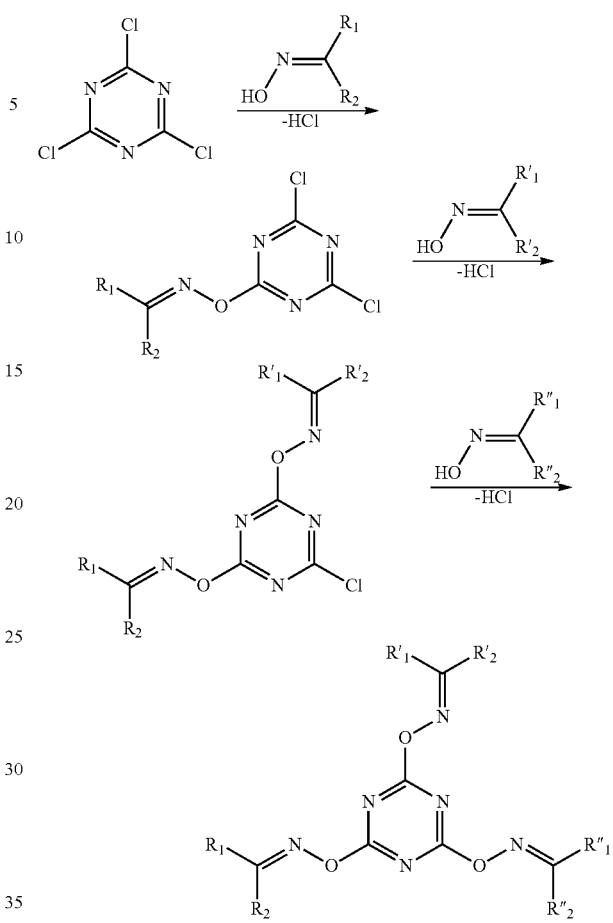

$R_1$ and $R_2$ have the definitions as given above, $R'_1$, $R'_2$, $R''_1$ and $R''_2$ are defined as $R_1$ and $R_2$, however indicate independently different meanings to show the case wherein $R_1$ and $R_2$ in all groups $R_1R_2C{=}N{-}O{-}$ in the compound of the formula I are different.

If n is 2, the intermediate used in the reaction is a compound

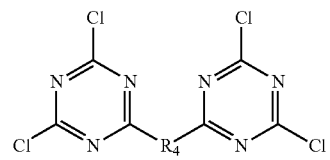

To prepare such intermediate the cyanuric chloride is reacted with 0.5 equivalents of the corresponding bis-nucleophile (diamine, aminoalcohol, diol etc.) at 0-10° C. It is well known that only one Cl-atom in cyanuric chloride is replaced at this low temperature.

The hydrogen chloride liberated during the reaction is conveniently scavenged by addition of a suitable inorganic or organic base. No limiting examples are $NaOHNa_2CO_3$, $K_2CO_3$, $Ca(OH)_2$, triethylamine or pyridine. From a process point of view it may be advantageous to use a base which forms with the HCl a liquid salt, a so called ionic liquid. A non limiting example of such base is e.g. 1-methylimidazole.

The reaction may be performed without solvent or in a suitable solvent or solvent mixture. Excess of the amine base can be used as a solvent or mixture of solvents like toluene, ethylacetate, dichloromethane, chlorobenzene, t-butyl-methylether can be used, to name just few examples. The reaction can be also run in water or in a biphasic system consisting of water and a solvent which is not miscible with water. Addition of a phase-transfer catalyst, for example an ammonium or phosphonium salt may be advantageous.

The reaction temperature is dictated by the reactivity of the employed halotriazine, oxime, solvent and base and may vary in a broad range, e.g. from −50 to 150° C., typically from 0 to 100° C.

Few examples of reactions of cyanuric chloride with oximes are reported in the literature, for example the reaction with acetophenone oxime [see *Furuya, Yoshiro; Ishihara, Kazuala; Yamamoto, Hisashi, Journal of the American Chemical Society* (2005), 127(32), 11240-11241] or acetone oxime [see *Chwalinsla; Stefan*, (1964), PL 48331, Priority: PL 19621128. CAN 62:43973] is disclosed Synthesis of iminoxytriazines from cyanuric chloride and oximes is the preferred method, however not the only one. For example, the symmetrical iminoxytriazines can be obtained from oximes and esters of cyanic acid as for example described by *Grigat, Ernst; Puetter, Rolf, Chemische Berichte* (1966), 99(7), 2361-70.

Synthesis of iminoxytriazines bearing one or two iminoxy groups can be achieved in a similar way. In this case, only one or two Cl-atoms of cyanuric chloride are substituted with the oxime derivative. The remaining Cl-atoms are then substituted with the desired nucleophile, for example with an amine, alcohol, phenol, cyanide or thiolate. It is also possible to first replace one or two Cl-atoms of cyanuric chloride with the desired nucleophile and then substitute the remaining Cl-atoms with the oxime derivative.

If an organic trialkylamine, is used as a base to scavenge the liberated HCl during the reaction of cyanuric chloride with the oxime then a fragment of this amine may replace one or two Cl atoms [see the preparation of the compound of example 13 below and *Beata Kolesinska, Zbigniew J. Kaminski, Tetrahedron* 65 (2009) 3573-3576].

The oxime derivatives $R_1R_2C=NOH$ used as starting materials in the above reactions are well known compounds, either commercially available or readily prepared by standard methods known by the person skilled in the art [see for example Chiba, S.; Narasaka, K., *Science of Synthesis, Knowledge Updates* (2011), (4), 445-499. *Georg Thieme Verlag*, CAN 156:637350].

Subject of the invention therefore also is

A process for the preparation of a compound of the formula I, wherein $R_1$ and $R_2$ independently of each other are hydrogen, $NH_2$, $NHR_5$, $NR_5R_6$, $COR_5$, $COOR_5$, $CONH_2$, $CONHR_5$, $CONR_5R_6$, $CN$, $SR_5$, $OR_5$, $C_1$-$C_{18}$alkyl, $C_3$-$C_{12}$cycloalkyl, $C_6$-$C_{14}$aryl or $C_2$-$C_{14}$heteroaryl, wherein said $C_3$-$C_{12}$cycloalkyl, $C_6$-$C_{14}$aryl or $C_2$-$C_{14}$heteroaryl is unsubstituted or substituted by one or more radicals selected from the group consisting of $C_1$-$C_{12}$alkyl, $C_3$-$C_{12}$-cycloalkyl, phenyl, halogen and $C_1$-$C_{12}$ alkoxy, or $R_1$ and $R_2$ together with the C atom to which they are linked form a 4 to 12 membered carbocyclic or heterocyclic saturated or unsaturated ring which is unsubstituted or substituted by one or more radicals selected from the group consisting of $C_1$-$C_{12}$alkyl, $C_3$-$C_{12}$-cycloalkyl, phenyl, halogen and $C_1$-$C_{12}$ alkoxy;

$R_3$ is $R_2C=N-O-$;

if n is 1, $R_4$ is F, Cl, OH, $OR_5$, SH, $SR_5$, $NH_2$, $NHR_5$, $NR_5R_6$ or $R_1R_2C=N-O-$;

wherein $R_1$ and $R_2$ in all groups $R_1R_2C=N-O-$ in the compound of the formula I are identical or different;

if n is 2, $R_4$ is a difunctional group derived from a diol, diamine, aminoalcohol or mercaptoalcohol;

$R_5$ and $R_6$ independently of each other are $C_1$-$C_{18}$alkyl, $C_3$-$C_{12}$cycloalkyl, $C_6$-$C_{14}$aryl or $C_2$-$C_{14}$heteroaryl;

provided that (i) if $R_4$ is $R_1R_2C=N-O-$, $R_1$ and $R_2$ together with the C atom to which they are linked do not form unsubstituted cyclohexyl or unsubstituted cyclododecyl;

(ii) if $R_4$ is $R_1R_2C=N-O-$, $R_1$ and $R_2$ are not both methyl;

(iii) if $R_4$ is $R_1R_2C=N-O-$, and $R_1$ is methyl, $R_2$ is not phenyl;

(iv) if $R_1$ and $R_2$ are both methyl, or if $R_1$ and $R_2$ together with the C atom to which they are linked form unsubstituted cyclohexyl or unsubstituted cyclododecyl, $R_4$ is not Cl;

(v) if $R_1$ and $R_2$ are both methyl and $R_4$ is $OR_5$, $R_5$ is not 4-methyl-coumarin-7-yl; by reacting trichloro-1,3,5-triazine, tribromo-1,3,5-triazine or triiodo-1,3,5-triazine with 3 oxime compounds of the formula (II)

(II)

wherein $R_1$ and $R_2$ are as defined above.

The compounds of formula (I) are used as polymerization initiators, polymerization auxiliaries or molecular weight modifiers in polymerizable compositions comprising at least one ethylenically unsaturated, polymerizable monomer or oligomer, preferably in polymerizable compositions used for preparing coatings.

The invention therefore provides a composition comprising (a) an ethylenically unsaturated, polymerizable monomer or oligomer and (b) at least one compound of formula (I) in an effective, thermally or actinically radicals generating amount.

In the composition according to the invention the amount of functional groups $R_1R_2C=N-O-$ in the compound of formula I in component (b) is from 0.01 to 30, preferably from 0.05 to 10, particularly preferably from 0.1 to 5.0 per 100 ethylenically unsaturated functional groups $C=C$ of the polymerizable monomer or oligomer (a).

It is sufficient for the instant polymerization that each one of the components (a) and (b) are present. However, it is generally useful to use a mixture of more than one components (a), for example from 2 to 100 components (a). In particular, oligomers are usually mixtures of components having different molecular weights. More than one components (b) can also advantageously be used, for example from 2 to 100 components (b). When more than one components (b) are used, they can have similar or different reactivities, in the latter case enabling stepwise polymerisation. It is also possible to add further components (a) and/or (b) at any stage after the polymerization has been started.

Oligomers in the sense of the invention are compounds obtainable by linking together from 2 to about 50, preferably from 3 to 20 ethylenically unsaturated units, which compounds still comprise at least one ethylenically unsaturated double bond and usually have a molecular weight of from 150 to 5000 Da.

Ethylenically unsaturated, polymerizable monomers or oligomers are generally known radically polymerizable compounds having at least one ethylenically unsaturated double bond, including monomers, prepolymers, oligomers and copolymers of any thereof. Non-limiting examples of such monomers include:

- ethylenically unsaturated polymerizable monomers selected from the group consisting of alkenes, conjugated dienes, styrenes, acrolein, vinyl acetate, vinylpyrrolidone, vinylimidazde, maleic anhydride, acrylic acid, acrylic acid derivatives, vinyl halides and vinylidene halides, such as ethylene, isoprene, 1,3-butadiene and $\alpha$-$C_5$-$C_{i8}$alkenes, styrene and styrenes substituted on the phenyl group by from one to three substituents selected from the group consisting of hydroxy. $C_1$-$C_4$alkoxy, e.g. methoxy or ethoxy, halogen, e.g. chlorine, amino and $C_1$-$C_4$alkyl, e.g. methyl or ethyl, such as methyl styrene, chloromethyl styrene, o-, m-, or p-hydroxystyrene;
- unsaturated carboxylic acids such as acrylic acid, methacrylic acid, crotonic acid, itaconic acid, maleic acid, or fumaric acid and salts, esters and amides thereof, as well as unsaturated fatty acids such as linolenic acid and oleic acid, acrylic and methacrylic acid being preferred; such unsaturated carboxylic acids optionally being used in admixture with saturated di- or poly-carboxylic acids, such as malonic acid, succinic acid, glutaric acid, adipic acid, sebacic acid, 1,4-cyclohexane dicarboxylic acid, tetrachlorophthalic acid, tetrabromophthalic acid, phthalic anhydride, tetrahydrophthalic acid, isophthalic acid, terepthalic acid, trimellitic acid, heptanedicarboxylic acid, dodecanedicarboxylic acid orhexahydrophthalic acid;
- unsaturated carboxylic acid esters derived from above-mentioned unsaturated carboxylic acids and mixtures of unsaturated carboxylic acids, wherein the esters are for example alkyl esters such as methyl, ethyl, 2-chloroethyl, N-dimethylaminoethyl, n-butyl, isobutyl-, pentyl, hexyl, cyclohexyl, 2-ethylhexyl, octyl, isobornyl or [2-exobornyl]esters; benzyl esters; phenyl, benzyl or o-, m- and p-hydroxy-phenyl esters; hydroxy alkyl esters such as 2-hydroxyethyl, 2-hydroxypropyl, 4-hydroxybutyl, 3,4-dihydroxybutyl or glycerol[1,2,3-propanetriol]esters; epoxy alkyl esters such as glycidyl, 2,3-epoxybutyl, 3,4-epoxy butyl, 2,3-epoxycyclohexyl or 10,11-epoxyundecyl esters; amino alkyl or mercapto alkyl esters; or polyfunctional esters as described below;
- unsaturated carboxylic acid amides derived from above-mentioned unsaturated carboxylic acids and mixtures of unsaturated carboxylic acids, wherein the amide groups may be similar as for above-mentioned esters, for example (meth)acryl amides or N-substituted (meth)acryl amides such as N-methylolacrylamide, N-methylolmethacrylamide, N-ethylacryamide, N-ethylmethacrylamide, N-hexylacrylamide, N-hexylmethacrylamide, N-cyclohexylacrylamide, N-cyclohexylmethacrylamide, N-hydroxyethylacrylamide, N-phenylacrylamide, N-phenylmethacrylamide, N-benzylacrylamide, N-benzylmethacrylamide, N-nitrophenylacrylamide, N-nitrophenylmethacrylamide, N-ethyl-N-phenylacrylamide, N-ethyl-N-phenylmethacrylamide, N-(4-hydroxyphenyl)acrylamide, and N-(4-hydroxyphenyl)methacrylamide or IBMAA (N-isobutoxymethyl acrylamide, or amides with aliphatic polyvalent amines;
- (Meth)acrylnitriles;
- unsaturated acid anhydrides such as itaconic anhydride, maleic anhydride, 2,3-dimethyl maleic anhydride or 2-chloromaleic anhydride;
- vinyl ethers such as isobutyl vinyl ether, ethyl vinylether, 2-chloroethyl vinylether, hydroxyethyl vinylether, propyl vinylether, butyl vinylether, isobutyl vinyl ether, octyl vinylether or phenyl vinylether;
- vinyl esters such as vinyl acetate, vinyl chloroacetate, vinyl butyrate and vinyl benzoate;
- vinyl chloride or vinylidene chloride;
- N-vinyl heterocyclic compounds, such as N-vinylpyrrolidone or suitably substituted vinylpyrrolidones, N-vinylcarbazol or 4-vinylpyridine;
- diacrylate esters such as 1,6-hexane diol diacrylate (HDDA), ethylene glycol diacrylate, propylene glycol diacrylate, tripropylene glycol diacrylate, neopentyl glycol diacrylate, hexamethylene glycol diacrylate and bisphenol A diacrylate;
- divinylbenzene, divinyl succinate, diallyl phthalate, triallyl phosphate, triallyl iso-cyanurate or tris(2-acryloylethyl) isocyanurate;
- esters of multifunctional alcohols, for example aromatic polyols such as hydroquinone, 4,4'-dihydroxydiphenyl, 2,2-di(4-hydroxyphenyl)propane, novolaks or resols, or, especially, aliphatic and cycloaliphatic polyols including e.g. alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris($\beta$-hydroxyethyl)amine, trimethylolethane, trimethylolpropane, pentaerythritol, dipentaerythritol and sorbitol, these polyols being optionally partially or fully esterified by one or by different unsaturated carboxylic acid(s), it being possible for the free hydroxyl groups in partial esters to be modified, for example etherified, or esterified by other carboxylic acids; or esters of polyepoxides based on these polyols, especially from aromatic polyols and epichlorohydrin, as well as polymers and copolymers that contain hydroxyl groups in the polymer chain or in side groups, such as polyvinyl alcohol and copolymers thereof, polymethacrylic acid hydroxyalkyl esters or copolymers thereof, or oligoesters having hydroxyl terminal groups; such as trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates or methacrylates, glycerol di- or tri-acrylate, 1,4-cyclohexane diacrylate, bisacrylates or bismethacrylates of polyethylene glycol having a molecular weight of from 200 to 1500 Da, dipropylene glycol diacrylate, tripropylene glycol diacrylate, glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate or neopentyl glycol propoxylate diacrylate;

non limiting examples of higher molecular weight (oligomeric) polyunsaturated compounds (also known as prepolymers) are esters of ethylenically unsaturated mono- or poly-functional carboxylic acids as described above and polyols or polyepoxides; polymers having ethylenically unsaturated groups in the chain or in side groups, such as unsaturated polyesters, polyamides and polyurethanes and copolymers thereof; alkyd resins; polybutadiene or butadiene copolymers, polyisoprene or isoprene copolymers, polymers or copolymers having (meth)acrylic groups in side chains such as methacrylated urethanes or also mixtures of one or more such polymers; or aminoacrylates; or mixtures of any number of any thereof in any proportions, independently from their functionality, optionally in combination with further reactive components such as so-called aminoacrylates, that is, oligomers based on acrylates which has been modified by reaction with primary or secondary amines, as described, for example, by Gaske in U.S. Pat. No. 3,844, 916, by Weiss et al. in EP0280222, by Meixner ef al, in U.S. Pat. No. 5,482,649 or by Reich et al. in U.S. Pat. No. 5,734,002. Commercial aminoacrylates are, for example, Ebecryl® 80, Ebecryl® 81, Ebecryl® 83, Ebecryl® P115, Ebecryl® 7100 (UCB Chemicals), Laromer® PO 83F, Laromer® PO 84F, Laromer® PO 94F (BASF), Photomer® 4775 F, Photomer® 4967 F (BASF Cognis) CN501™, CN503™ or CN550™ (Cray Valley). Polymers, preferably coatings, may advantageously be prepared from the instant compositions. To prepare a polymer, preferably a coating, the components (a) and (b) of the formulation and optionally colourants and/or additives are applied uniformly to a substrate by means of known coating techniques, for example by spin-coating, immersion, knife coating, curtain pouring, brush application or spraying, especially by electrostatic spraying and reverse-roll coating, or also by electrophoretic deposition. The quantity applied (coating thickness) and the nature of the substrate (layer support) are dependent on the desired field of application. The coating thicknesses are generally comprised in the range of from 0.1 μm to more than 300 μm, though the coatings may if desired also be thicker, for example 1-5 mm.

The wet coatings are then cured by polymerization as described below.

The instant coatings should be understood also to comprise printing inks (as long as wet) and prints (dry after curing).

Depending on their specific composition, the coatings can be applied as printing inks, liquid coatings, powder coatings, gelcoats, adhesives, photoresists on any desired substrate. Suitable are substrates of any kind, for example wood, textiles, paper, ceramics, glass, glass fibres, plastics such as polyester, polyethylene terephthalate, polyolefins or cellulose acetate, especially in the form of films, and also metals such as Al, Cu, Ni, Fe, Zn, Mg, Co, GaAs, Si or $SiO_2$, to which there can be applied a protective or, decorative layer, if desired by imagewise exposure and/or on an already existing coating, such as a primer.

The composition may further be used in moulding processes.

The above-described compositions may further comprise customary additives, which may, as an alternative, also be added after the polymerization. Such additives can be added in usual small amounts, e.g. UV-absorbers or light stabilizers, e.g. compounds selected from the group consisting of hydroxyphenylbenzotriazoles, hydroxyphenylbenzophenones, oxalamides and hydroxyphenyl-s-triazines. Particularly suitable light stabilizers are those selected from the group consisting of sterically hindered amines (HALS), e.g. of the 2-(2-hydroxyphenyl)-1,3,5-triazine or 2-hydroxyphenyl-2H-benzotriazole type. Examples of light stabilizers of the 2-(2-hydroxyphenyl)-1,3,5-triazine type are known for example from U.S. Pat. No. 4,619,956, EP0434608, U.S. Pat. No. 5,198,498, U.S. Pat. No. 5,322,868, U.S. Pat. No. 5,369, 140, U.S. Pat. No. 5,298,067, WO94/18278, EP0704437, GB2297091 or WO96/28431.

Examples of colourants are pigments or dyes, especially pigments, in particular organic pigments such as those listed in the Colour Index.

Accordingly, the composition may comprise at least one pigment, at least one dye or a mixture of at least one pigment and at least one dye.

The compositions may further comprise other customary additives, e.g. fillers such as calcium carbonate, silicates, glass or glass fibre material, talcum, kaolin, mica, barium sulphate, metal oxides and hydroxides, carbon black, graphite, pulverized wood and pulverized or fibrous material from other natural products, synthetic fibres, plasticizers, lubricants, emulsifiers, pigments, fluidizers, catalysts, optical brighteners, flame retardants, antistatics or blowing agents.

The invention also pertains to the use of the instant compounds of formula (I) to generate radicals in reactions triggered by the presence of radicals, as well as a process for preparing polymeric matter, preferably in the form of coatings, by using compositions comprising compounds of formula (I).

The invention further provides a process for preparing the above-described oligomer, cooligomer, polymer or copolymer by free-radical polymerization using the above-described compounds of formula (I).

The compounds of formula (I) may be used as polymerization initiators, especially as thermal radical initiators (TRI) in a curing agent for coatings that cure by free radical polymerization.

The coating may be a thermal curing composition, a dual curable composition (thermal and UV-radiation or thermal and e-beam radiation) or a hybrid curable composition (radically and cationically curing components).

Dual cure compositions are cured first by heat and subsequently by UV or electron irradiation, or vice versa. The compositions contain components with ethylenic double bonds as described above capable to react on irradiation with UV light in presence of a compound of the formula (I).

Hybrid systems contain cationically and radically polymerisable and photopolymerisable raw materials. Examples of cationically polymerisable systems include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. Radiation curable resins contain ethylenically unsaturated compounds, especially (meth)acrylate resins. Examples are also as given above.

Furthermore interesting are hybrid systems that are photopolymerized in a first stage and then crosslinked through thermal post-treatment in a second stage or vice versa. Such hybrid systems comprise an unsaturated compound in admixture with non-photopolymerizable film-forming components. These may, for example, be physically drying polymers or solutions thereof in organic solvents, for example nitrocellulose or cellulose acetobutyrate. However, they may also be chemically or thermally curable resins, for example polyisocyanates, polyepoxides or melamine resins.

Free radical polymerization includes thermal polymerisation, including thermal curing, IR-curing and NIR-curing, and/or UV polymerisation.

Thermal curing refers to the application of convection heat or IR- or NIR-radiation or microwave irradiation or ultrasound exposure after the mixture has been applied to the substrate. In case of powder coatings, the adhered powder coating is first melted to form a surface layer preferably by convection heat. Suitable temperatures to initiate and complete free-radical polymerization are for example temperatures of from 50° C. to 250° C., especially 60-180° C.

The NIR radiation used in the process according to the invention is short-wave infrared radiation in the wavelength range from about 750 nm to about 1500 nm, preferably from 750 nm to 1200 nm. Radiation sources for NIR radiation include, for example, conventional NIR radiation emitters, which are available commercially (for example, from Adphos).

The IR radiation used in the process according to the invention is medium wave radiation in the wave length range from about 1500 nm to about 3000 nm and/or longer-wave infrared radiation in the wave length range above 3000 nm. Such IR radiation emitters are available commercially, too (for example, from Heraeus).

The microwave radiation used for the curing process is electromagnetic radiation in the wavelength from about 1 mm to 30 cm.

Ultrasound curing is performed with a frequency above 20 kHz.

The UV-curing step is carried out usually using light of wavelengths from about 150 m into the IR range, e.g. from about 200 nm to about 650 nm, especially from 200 nm to 450 nm. As light sources there are used a large number of the most varied types. Both point sources and platform radiators (lamp arrays) are suitable. Examples are: carbon arc lamps, xenon arc lamps, medium-pressure, high-pressure and low-pressure mercury radiators doped, where appropriate, with metal halides (metal halide lamps), microwave-excited metal vapour lamps, excimer lamps, superactinic fluorescent tubes, fluorescent lamps, argon incandescent lamps, electronic flash lamps, e.g. high-energy flash lamps, photographic floodlight lamps, electron beams and X-rays generated by means of synchrotrons or laser plasma. Alternatively, the actinic radiation is provided by light emitting diodes (LED) or organic light emitting diodes (OLEO), e.g. UV light emitting diodes (UV-LED). Said LEDs allow instant on and off switching of the radiation source. Further. UV-LEDs generally have a narrow wavelength distribution and offer the possibility to customize the peak wavelength and also provide an efficient conversion of electric energy to UV radiation.

The invention further provides a generally applicable, process for the controlled degradation of polyolefins wherein the compounds of formula (I) are used to lower the molecular weight of polyolefins, preferably polypropylene, propylene copolymers or polypropylene blends.

In the instant degradation process, the compounds of formula (I) are adequately incorporated into the polyolefin to be degraded in concentrations of from about 0.001 to 5.0% by weight, preferably from 0.01 to 2.0% by weight and particularly preferably from 0.02 to 1.0% by weight, based on the total weight of the polyolefin to be degraded. Such amounts are effective for desirably reducing the molecular weight. The compounds of formula (I) can be added as individual compounds or as mixtures to the polyolefin to be degraded. The polyolefin-type polymers to be degraded encompass in particular propylene homopolymers, propylene copolymers and polypropylene blends. Propylene copolymers may be build up from olefin mixtures comprising propylene and various proportions of comonomers, generally up to 90% by weight, preferably up to 50% by weight of comonomers, based on the olefin mixture. Examples of comonomers are olefins such as 1-olefins, e.g. ethylene, 1-butene, isobutylene, 1-pentene, 1-hexene, 1-heptene or 1-octene; cycloolefins, e.g. cyclopentene, cyclohexene, norbornene or ethylidenenorborne; dienes such as butadiene, isoprene, 1,4-hexadiene, cyclopentadiene, dicyclopentadiene or norbornadiene; acrylic acid derivatives; or unsaturated carboxylic anhydrides such as maleic anhydride. Polypropylene blends which can be used are mixtures of polypropylene with poly-olefins. Examples are blends of polypropylene with polyethylenes such as high density polyethylene (HDPE), high molecular weight high density polyethylene (HMW HDPE), ultra high molecular weight high density polyethylene (UHMW HDPE), medium density polyethylene (MDPE), low density polyethylene (LDPE), linear low density polyethylene (LLDPE), branched low density polyethylene (BLDPE) or ethylene-propylene-diene terpolymers (EPDM) containing small proportions of diene.

Incorporation into the polymers can be carried out, for example, by mixing the compounds of formula (I) or mixtures thereof and, if desired, further additives into the polymers using the methods customary in process technology.

Incorporation can, alternatively, also be carried out at temperatures which do not yet cause decomposition of the polymers (latent compound). The polymers prepared in this way can subsequently be heated a second time and subjected to an elevated temperature for a sufficient period of time so that the desired polymer degradation occurs.

The examples which follow illustrate the invention in more detail, without restricting the scope said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

EXAMPLE 1

N-[[4,6-bis[(isopropylideneamino)oxy]-1,3,5-triazin-2-yl]oxy]propan-2-imine

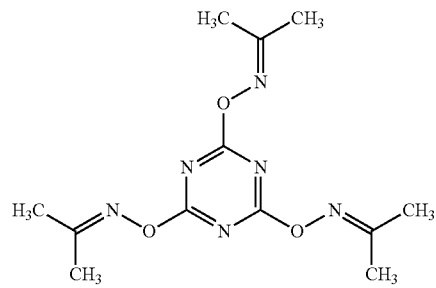 [SMILES: CC(C)=NOc1nc(ON=C(C)C)nc(ON=C(C)C)n1]

To a cold (0° C.) solution of acetone oxime (2.92 g, 0.04 mol) in dry pyridine (15 ml) is added cyanuric chloride (1.84 g, 0.01 mol). An exothermic reaction occurs and the temperature rises to 35° C. The solution is then stirred for 5 h at room temperature and then poured into 100 ml of ice-cold water. The resulting emulsion is extracted with dichloromethane (5×20 ml), the extracts are dried over $MgSO_4$ and the solvent is evaporated. The residue is chromatographed (silica gel, $CH_2Cl_2$—$C_2H_5O(CO)CH_3$ 7:3) and the pure fraction is recrystallized from dichloromethane-hexane to afford 2.79 g of the title compound as a white solid, mp. 156-158° C.

$^1$H-NMR ($CDCl_3$, 400 MHz, δ ppm): 2.066 (s, 3×$CH_3$), 2.022 (s, 3×$CH_3$).

$^{13}$C-NMR (CDCl$_3$, 101.61 MHz, δ ppm): 173.87, 164.15, 21.94, 17.22.

EXAMPLE 2

N-[[4-[(E)-1-methylpropylideneamino]oxy-6-[(Z)-1-methylpropylideneamino]oxy-1,3,5-triazin-2-yl]oxy]butan-2-imine

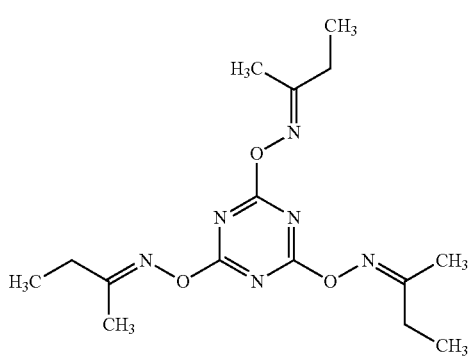 [SMILES: CC/C(C)=N\Oc1nc(O/N=C(\C)CC)nc(O/N=C(\C)CC)n1]

To a cold (0° C.) solution of ethylmethyl-ketoxime (4.18 g, 0.048 mol) in dry pyridine (16 ml) is added cyanuric chloride (2.21 g, 0.012 mol). An exothermic reaction occurs and the temperature rises to 16° C. The solution is then stirred 12 h at room temperature and then poured into 150 ml of ice-cold water. The resulting emulsion is extracted with dichloromethane (3×30 ml), the extracts are dried over MgSO$_4$ and the solvent is evaporated. The residue is chromatographed (silica gel, CH$_2$Cl$_2$—C$_2$H$_5$O(CO)CH$_3$ 8:3) to afford 3.72 g of the title compound as a colorless oil which slowly solidifies on standing, mp. 51-56° C.

$^1$H-NMR (CDCl$_3$, 400 MHz, δ ppm): mixture of isomers, 2.53 (q, CH$_2$CH$_3$), 2.37 (q, CH$_2$CH$_3$), 2.05 (s, CH$_3$), 2.03 (s, CH$_3$), 1.13 (s, CH$_2$CH$_3$), 1.08 (s, CH$_2$CH$_3$).

$^{13}$C-NMR (CDCl$_3$, 101.61 MHz, δ ppm): mixture of isomers, 174.10, 167.95, 167.92, 29.19, 23.95, 19.50, 15.25, 10.74, 10.24.

EXAMPLE 3

N-[[4,6-bis[(cyclohexylideneamino)oxy]-1,3,5-triazin-2-yl]oxy]cyclohexanimine

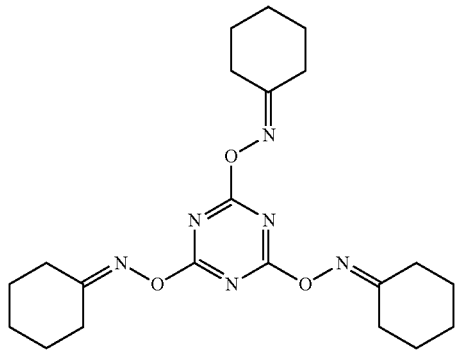 [SMILES: C1CCC(=NOc2nc(ON=C3CCCCC3)nc(ON=C3CCCCC3)n2)CC1]

To a cold (0° C.) solution of cyclohexanone oxime (4.53 g, 0.04 mol) in dry pyridine (20 ml) is added cyanuric chloride (1.84 g, 0.01 mol). An exothermic reaction occurs and the temperature rises to 22° C. The solution is then stirred 15 h at room temperature and then poured into 200 ml of ice-cold water. The precipitated solid is filtered off, dried and recrystallized from dichloromethane-hexane to afford 3.57 g of the title compound as a white solid. The compound decomposes without melting above 120° C. (DSC data).

$^1$H-NMR (CDCl$_3$, 400 MHz, δ ppm): 2.67 (m, 3×CH$_2$), 2.40 (m, 3×CH$_2$), 1.80-1.50 (m, 9×CH$_2$).

$^{13}$C-NMR (CDCl$_3$, 101.61 MHz, δ ppm): 174.07, 168.81, 32.05, 27.03, 26.71, 25.76, 25.37.

EXAMPLE 4

1-phenyl-N-[[4-[(Z)-1-phenylethylideneamino]oxy-6-[(E)-1-phenylethylideneamino]oxy-1,3,5-triazin-2-yl]oxy]ethanimine

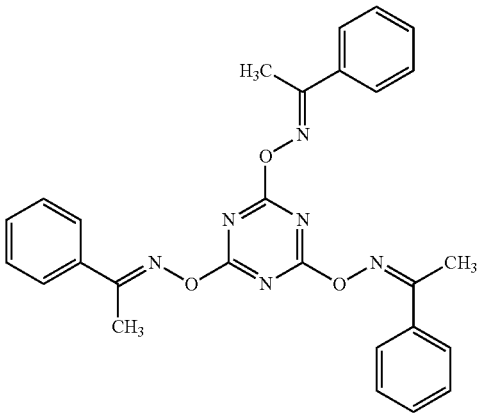 [SMILES: C/C(=N/Oc1nc(O/N=C(\C)c2ccccc2)nc(O/N=C(\C)c2ccccc2)n1)c1ccccc1]

The title compound is obtained in analogy to example 3 from acetophenone oxime (6.8 g, 0.05 mol) and cyanuric chloride (2.76 g, 0.015 mol) in 20 ml pyridine as a white solid, 5.71 g, mp. 153-156° C.

$^1$H-NMR (CDCl$_3$, 300 MHz, δ ppm): 7.87-7.83 (m, 3×2ArH), 7.49-7.39 (m, 3×3ArH), 2.53 (s, 3×CH$_3$CO).

$^{13}$C-NMR (CDCl$_3$, 75.47 MHz, δ ppm): 174.41, 163.32, 134.73, 130.67, 128.55, 127.20, 14.73.

EXAMPLE 5

N-[[4,6-bis[(cyclododecylideneamino)oxy]-1,3,5-triazin-2-yl]oxy]cyclododecanimine

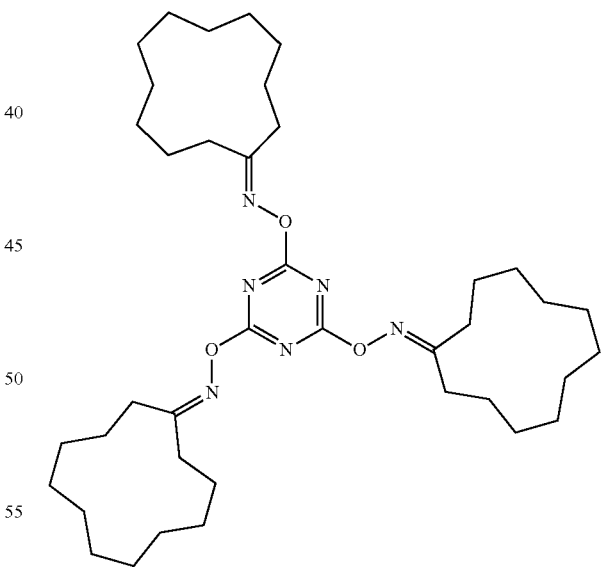

To a cold (0° C.) solution of cyclododecanone oxime (7.89 g, 0.04 mol) in dry pyridine (30 ml) is added cyanuric chloride (1.84 g, 0.01 mol). An exothermic reaction occurs and the temperature rises to 20° C. The solution is then stirred 20 h at room temperature and then poured into 300 ml of ice-cold water. The precipitated solid is filtered off and chromatographed (silica gel, CH$_2$Cl$_2$—C$_2$H$_5$O(CO)CH$_3$ 95:5). The pure fraction is recrystallized from ethylacetate-hexane to afford 2.36 g of the title compound as a white solid, m.p. 104-107° C.

¹H-NMR (CDCl₃, 400 MHz, δ ppm): 2.59 (m, 3×CH₂), 2.47 (m, 3×CH₂), 1.80-1.30 (m, 27×CH₂).
¹³C-NMR (CDCl₃, 101.61 MHz, δ ppm): 174.10, 170.05, 30.81, 27.23, 25.16, 24.81, 24.36, 24.12, 23.94, 23.39, 23.06, 23.00, 22.62.

EXAMPLE 6

N-[[4,6-bis[[(Z)-(3,3,5-trimethylcyclohexylidene)amino]oxy]-1,3,5-triazin-2-yl]oxy]-3,3,5-trimethyl-cyclohexanimine

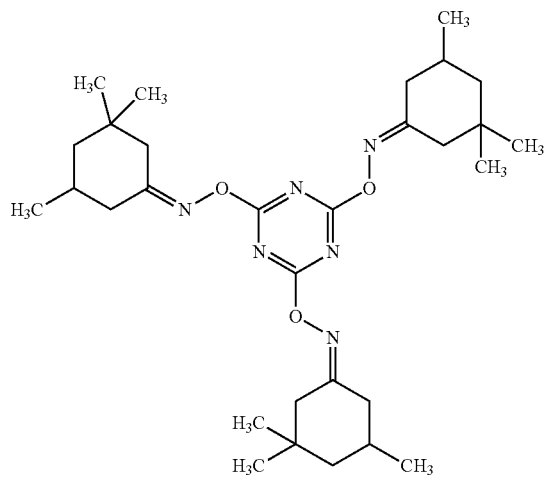

The title compound is obtained in analogy to example 5 from 3,5,5-trimethylcyclohexanone oxime (15.5 g, 0.1 mol) and cyanuric chloride (4.8 g, 0.026 mol) in 60 ml pyridine as a white solid, 4.7 g, mp. 164-200° C.

¹H-NMR (CDCl₃, 400 MHz, δ ppm): mixture of isomers, 3.45-1.00 (m, 9×CH₂), 1.01 (s, 3×CH₃), 0.95 (d, 3×CH₃), 0.82 (s, 3×CH₃),
¹³C-NMR (CDCl₃, 101.61 MHz, δ ppm): mixture of isomers, 174.00, 168.17, 168.04, 47.92, 47.72, 44.03, 44.01, 39.66, 39.27, 34.35, 34.20, 33.99, 32.01, 31.86, 29.51, 28.35, 25.44, 25.17, 22.19.

EXAMPLE 7

N'-[[4,6-bis[[(Z)-benzylideneamino]oxy]-1,3,5-triazin-2-yl]oxy]benz-amidine

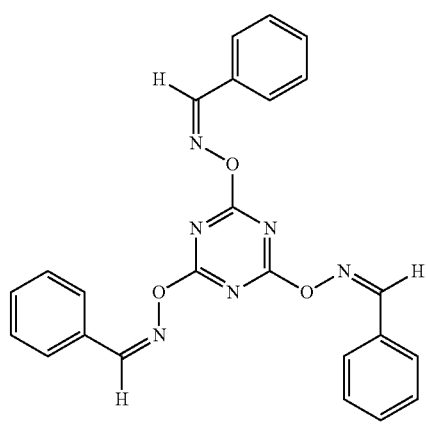 [SMILES: C(=N/Oc1nc(O/N=C\c2ccccc2)nc(O/N=C\c2ccccc2)n1)/c1ccccc1]

To a solution of benzaldehyde oxime (7.45 g, 0.0615 mol) in dry tetrahydrofurane (THF) (25 ml) is added triethylamine (6.27 g, 0.062 mol) and then at room temperature (RT) within 15 minutes the solution of cyanuric chloride (3.50 g, 0.019 mol) in 15 ml of THF. The thick suspension is diluted with additional 15 ml of THF and then stirred for 15 h at RT. Thereafter are added 400 ml of ice-cold water, the precipitated solid is filtered off, dried and then recrystallized twice from dichloromethane-ethylacetate to afford 4.29 g of the title compound as a white powder which does not melt below 300° C.

¹H-NMR (CDCl₃, 400 MHz, δ ppm): 8.59 (s, 3×PhCH=N), 7.81 (dd, 3×2ArH), 7.55-7.40 (m, 3×3ArH).
¹³C-NMR (CDCl₃, 101.61 MHz, δ ppm): 174.21, 156.84, 131.89, 129.76, 128.88, 128.67.

EXAMPLE 8

N'-[[4,6-bis[[(E)-[amino(phenyl)methylene]amino]oxy]-1,3,5-triazin-2-yl]oxy]benzamidine

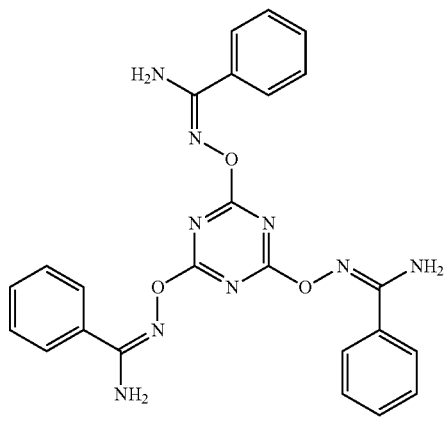 [SMILES: N/C(=N/Oc1nc(O/N=C(/N)c2ccccc2)nc(O/N=C(/N)c2ccccc2)n1)c1ccccc1]

To a solution of benzamide oxime (5.45 g, 0.040 mol) in dry THF (40 ml) is added triethylamine (4.05 g, 0.040 mol) and then at RT within 15 minutes the solution of cyanuric chloride (1.84 g, 0.010 mol) in 25 ml of THF. The thick suspension is then stirred for 3 h at RT. Thereafter are added 400 ml of ice-cold water, the precipitated solid is filtered off, dried and then washed thoroughly at room temperature with ethyl acetate (50 ml) and acetonitrile (25 ml) to afford 3.2 g of the title compound as a white powder, mp 204-206° C.

¹H-NMR (DMSO-d₆, 400 MHz, δ ppm): 7.77 (dd, 3×2ArH), 7.55-7.40 (m, 3×3ArH), 6.92 (bs, 3×NH₂).
¹³C-NMR (CDCl₃, 101.61 MHz, δ ppm): 174.41, 157.29, 132.14, 130.98, 128.81, 127.41.

EXAMPLE 9

1-methyl-N-[[4-[(E)-(1-methylpyrrolidin-2-ylidene)amino]oxy-6-[(Z)-(1-methylpyrrolidin-2-ylidene)amino]oxy-1,3,5-triazin-2-yl]oxy]pyrrolidin-2-imine

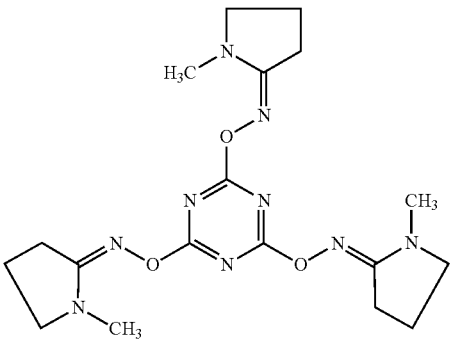 [SMILES: CN1CCC/C1=N/Oc1nc(O/N=C2/CCCN2C)nc(O/N=C2\CCCN2C)n1]

To a cold (0° C.) solution of N-methylpyrrolidine oxime (prepared as described by Eilingsfeld, Heinz; Seefelder, Matthias; Weidinger, Hans, Chemische Berichte (1963), 96(10), 2671-90) (8.6 g, 0.075 mol) in dry pyridine (45 ml) is added cyanuric chloride (3.87 g, 0.021 mol). An exothermic reaction occurs and the temperature rises to 16° C. The solution is stirred for 2 h at room temperature, then heated for 2 h at 44° C. and then evaporated to dryness under diminished pressure. The solid residue is washed with 10 ml water, dried and recrystallized twice from $C_2H_5OC$-Hexane to afford 6.9 g of the title compound as off white powder, mp. 173-176° C.

$^1$H-NMR (CDCl$_3$, 300 MHz, δ ppm): 3.39-3.31 (m, 3×CH$_2$), 2.95-2.85 (m, 3×CH$_2$), 2.92 (s, 3CH$_3$), 2.05-1.90 (m, 3×CH$_2$).

$^{13}$C-NMR (CDCl$_3$, 75.47 MHz, δ ppm): 173.89, 167.09, 53.01, 32.16, 28.15, 19.85.

LC-MS (APCI): for $C_{18}H_{27}N_9O_3$ [417.46], found M=417.3.

EXAMPLE 10

1-cyclohexyl-N-[[4-[(E)-(1-cyclohexylpyrrolidin-2-ylidene)amino]oxy-6-[(Z)-(1-cyclohexylpyrrolidin-2-ylidene)amino]oxy-1,3,5-triazin-2-yl]oxy]pyrolidin-2-imine

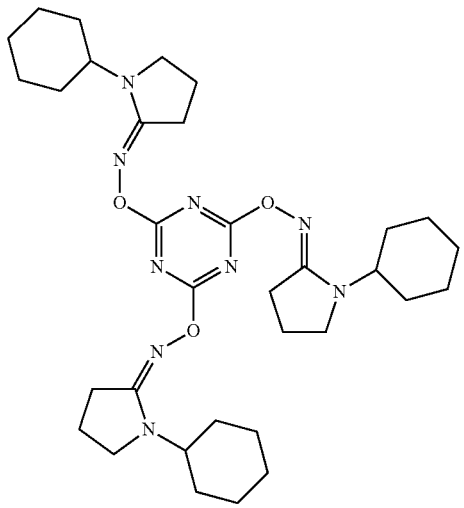 [SMILES: C1CCC(N2CCC/C2=N/Oc2nc(O/N=C3\CCCN3C3CCCCC3)nc(O/N=C3\CCCN3C3CCCCC3)n2)CC1]

N-Cyclohexylpyrrolidone-oxime: to a mixture consisting of chloroform (281 ml) and a 20 w % solution of phosgen in toluene (262.1 g, 0.53 mol) is added between 3-10° C. N-cyclohexyl-pyrrolidon (88.6 g, 0.53 mol). The resulting mixture is then stirred for 32 h at room temperature and directly used in the next step.

In a separate flask is placed aqueous 50% hydroxylamine (38.51 g, 0.583 mol) and water (74 ml). Into this solution is simultaneously under vigorous stirring added the phosgenated solution prepared before and a solution of NaOH (46.20 g, 1.155 mol) in 160 ml water. The temperature during the addition is kept between 10-20° C. The mixture is stirred at room temperature for additional 15 h, the organic layer is then separated, dried over MgSO$_4$ and evaporated. The solid residue is recristallized from ethylacetate-hexane to afford 38.4 g of N-cyclohexylpyrrolidone-oxime as an off white solid, mp. 142-145° C.

$^1$H-NMR (CDCl$_3$, 300 MHz, δ ppm): 8.5 bs (N=OH), 3.6-3.4 (m, 1H), 3.19 (t, CH$_2$), 2.68 (t, CH$_2$), 2.0-0.9 (m, 6×CH$_2$)

$^{13}$C-NMR (CDCl$_3$, 75.47 MHz, δ ppm): 161.76, 52.71, 45.05, 29.54, 26.39, 25.88, 25.66, 20.08.

GC-MS (Cl): for $C_{10}H_{18}N_2O$ [182.27]. found MH+=183.

To a cold (0° C.) solution of N-cyclohexylpyrrolidone-oxime (7.3 g, 0.04 mol) in dry pyridine (40 ml) is added cyanuric chloride (2.2 g, 0.012 mol). The mixture is then stirred for 20 h at room temperature and then poured into 400 ml of ice cold water. The solid precipitate is filtered off and recrystallized from dichloromethane-ethyl acetate-hexane to afford 6.05 g of the title compound as an off white crystals, mp. 156-160° C.

$^1$H-NMR (CDCl$_3$, 400 MHz, δ ppm): 3.95-3.80 (m, 3×1H), 3.40-3.25 (m, 3×CH$_2$), 2.95-2.80 (m, 3×CH$_2$), 2.0-1.0 (m, 18×CH$_2$).

$^{13}$C-NMR (CDCl$_3$, 100.61 MHz, δ ppm): 173.85, 166.38, 52.27, 45.27, 29.68, 28.59, 25.68, 25.32, 19.74.

EXAMPLE 11

N-[[4,6-bis[[(1,3-dimethylimidazolidin-2-ylidene)amino]oxy]-1,3,5-triazin-2-yl]oxy]-1,3-dimethyl-imidazolidin-2-imine

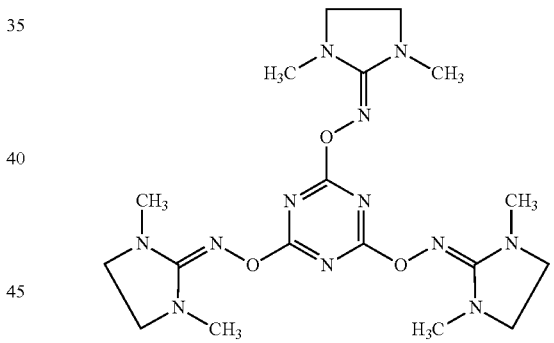

To a cold (0° C.) solution of 1,3-dimethyl-2-imidazolidinone oxime (prepared according Kitamura, Mitsuru; Chiba, Shunsuke; Narasaka, Koichi, Bulletin of the Chemical Society of Japan (2003), 76(5), 1063-1070) (5.3 g, 0.041 mol) in dry pyridine (25 ml) within 15 minutes is dropwise added cyanuric fluoride (1.49 g, 0.011 mol). The mixture is then heated for 2 h at 42° C. and then stirred for 15 h at room temperature. The pyridine is evaporated under reduced pressure, the residue is chromatographed (silica gel, CH$_2$Cl$_2$—CH$_3$OH 20:1 to 10:1) and the pure fractions are crystallized from ethyl acetate hexane to afford 2.4 g of the title compound as white crystalls, mp. 143-145° C. (decomposition).

$^1$H-NMR (CDCl$_3$, 300 MHz, δ ppm): 3.35-3.20 (m, 3×CH$_2$CH$_2$), 3.19 (s, 3×CH$_3$), 2.79 (s, 3×CH$_3$).

$^{13}$C-NMR (CDCl$_3$, 75.47 MHz, δ ppm): 174.07, 160.00, 51.21, 49.06, 37.75, 34.11.

LC-MS (APCI) for $C_{18}H_{30}N_{12}O_3$ [462.52] found M=462.

EXAMPLE 12

(3Z)-3-[[4,6-bis[[(Z)-(1-methyl-2-oxo-propylidene)amino]oxy]-1,3,5-triazin-2-yl]oxyimino]butan-2-one

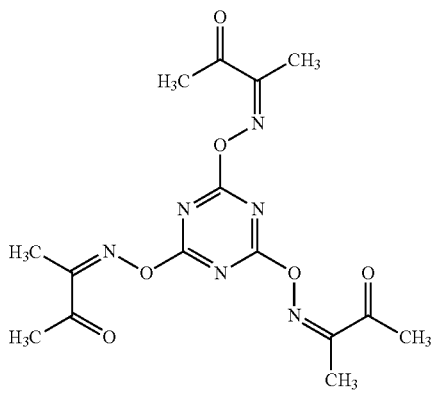 [SMILES: CC(=O)/C(C)=N\Oc1nc(O/N=C(/C)C(C)=O)nc(O/N=C(/C)C(C)=O)n1]

To a cold (0° C.) solution of 2,3-butandione-monoxime (12.13 g, 0.012 mol) in dry pyridine (35 ml) is dropwise added a solution of cyanuric chloride (5.53 g, 0.03 mol) in 15 ml tetrahydrofurane. The temperature of the reaction mixture at the end of the addition rises up to 55° C. The thick mixture is then stirred for 15 h at room temperature and then poured into 1000 ml of ice cold water. The precipitated sold is filtered off and recrystallized from $CH_2Cl_2$-ethyl acetate and then from $CH_2Cl_2$-hexane to afford the 4.68 g of the title compound as an off-white powder, mp 173-174° C.

$^1$H-NMR (CDCl$_3$, 400 MHz, δ ppm): 2.58 (s, 3×CH$_3$), 2.25 (s, 3×CH$_3$), $^{13}$C-NMR (CDCl$_3$, 101.61 MHz, δ ppm): 195.13, 174.20, 162.15, 25.67, 10.60.

EXAMPLE 13

N,N-diethyl-4,6-bis[(isopropylideneamino)oxy]-1,3,5-triazin-2-amine

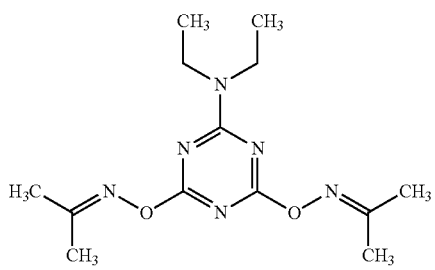 [SMILES: CCN(CC)c1nc(ON=C(C)C)nc(ON=C(C)C)n1]

To a solution of acetone oxime (4.68 g, 0.063 mol) and cyanuric chloride (3.69 g, 0.020 mol) in dry acetonitrile (40 ml) is at room temperature added triethylamine (6.38 g, 0.063 mol). The temperature of the reaction mixture at the end of the addition rises up to 44° C. The mixture is then stirred for 21 h at 45° C., cooled to 8° C., the precipitated solid is filtered off and the filtrate is evaporated under reduced pressure. The residue is washed thoroughly with water and dried to afford 2.96 g of the title compound as a white solid, mp. 111-113° C.

$^1$H-NMR (CDCl$_3$, 400 MHz, δ ppm): 3.66-3.60 (q, 2×C$H_2$CH$_3$), 2.07 (s, 2×CH$_3$), 2.03 (s, 2×CH$_3$), 1.17-1.13 (t, 2×CH$_2$C$H_3$).

$^{13}$C-NMR (CDCl$_3$, 75.47 MHz, . . . ppm): 172.58, 166.72, 162.37, 41.14, 22.09, 17.13, 12.96.

EXAMPLE A1

Polymerization of a Coating Composition

The following unsaturated polymerizable compositions are used (w/w %);

| Ingredients | Coating A | Coating B | Coating C |
|---|---|---|---|
| urethane-acrylate (Ebecryl 4858, Cytec) | 45.0% | | |
| hexafunctional-urethane acrylate (Ebecryl 1290, Cytec) | 15.0% | | |
| pentaerhytritol-[5EO]-tetraacrylate (Photomer 4172F, Cognis) | 39.5% | | |
| leveling additive (Efka 3299, BASF) | 0.5% | | |
| unsaturated-polyester blend (Palatal P6-01, DSM) | | 100% | |
| bis-A-epoxy-vinylester @ 60% in styrene (At-lac 430, DSM) | | | 100% |

1% w/w of a compound to be tested is dissolved in this composition and the resulting mixture is submitted to Differential scanning calorimetry (DSC) measurement. The activity of the tested compound is manifested by the exothermic curing reaction which is characterized by the Onset, Peak and Endset temperatures as well as the amount of heat liberated (exotherm reaction).

The following DSC parameters are used:

Apparatus: DSC 30 (Mettler)

Temperature Gradient: 5° C./Min

Temperature Range: 30-300° C.

Measurement under Nitrogen, flow rate 5 ml/Min

Sample amount: approx. 10 mg compound in an aluminum crucible.

The tested compounds and the results of the tests are listed in table 2.

TABLE 2

Polymerization of a coating: DSC evaluation

| Compound of example | | Onset temp. ° C. | Peak temp. ° C. | Endset temp. ° C. | Exotherm (Enthaplpy in J/g) |
|---|---|---|---|---|---|
| none | | no | no | no | 0 |
| 1 | 1 wt. % in "coat A" | 98 | 137 | 170 | 246 |
| 2 | 1 wt. % in "coat A" | 107 | 143 | 170 | 210 |
| 3 | 1 wt. % in "coat A" | 104 | 145 | 180 | 211 |
| 4 | 1 wt. % in "coat A" | 110 | 147 | 185 | 206 |
| 5 | 1 wt. % in "coat A" | 100 | 130 | 145 | 366 |
| | 3 wt. % in "coat A" | 90 | 118 | 140 | 378 |
| 6 | 1 wt. % in "coat B" | 90 | 142 | 170 | 158 |
| | 1 wt. % in "coat C" | 114 | 134 | 170 | 164 |
| 9 | 1 wt. % in "coat A" | 100 | 136 | 160 | 220 |
| | 3 wt. % in "coat A" | 90 | 115 | 150 | 200 |
| 10 | 1 wt. % in "coat B" | 60 | 124 | 145 | 250 |
| | 1 wt. % in "coat C" | 114 | 134 | 170 | 165 |
| 13 | 1 wt. % in "coat A" | 90 | 134 | 160 | 197 |
| | 3 wt. % in "coat A" | 85 | 128 | 160 | 230 |

The results summarized in the Table 2 show that no curing occurs with the blank formulation but that distinct exothemic curing is observed when compounds of the invention are incorporated.

The invention claimed is:
1. A composition comprising
(a) an ethylenically unsaturated, polymerizable monomer or oligomer and
(b) as radical generating compound an iminoxytriazine compound of the formula I

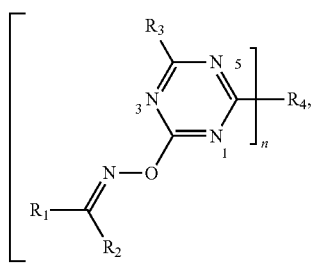

wherein
n is 1 or 2;
$R_1$ and $R_2$ independently of each other are hydrogen, $NH_2$, $NHR_5$, $NR_5R_6$, $COR_5$, $COOR_5$, $CONH_2$, $CONHR_5$, $CONR_5R_6$, CN, $SR_5$, $OR_5$, $C_1$-$C_{18}$alkyl, $C_3$-$C_{12}$cycloalkyl, $C_6$-$C_{14}$aryl or $C_2$-$C_{14}$heteroaryl,
wherein said $C_3$-$C_{12}$cycloalkyl, $C_6$-$C_{14}$aryl or $C_2$-$C_{14}$heteroaryl is unsubstituted or substituted by one or more radicals selected from the group consisting of $C_1$-$C_{12}$alkyl, $C_3$-$C_{12}$-cycloalkyl, phenyl, halogen and $C_1$-$C_{12}$ alkoxy,
or $R_1$ and $R_2$ together with the C atom to which they are linked form a 4 to 12 membered carbocyclic or heterocyclic saturated or unsaturated ring which is unsubstituted or substituted by one or more radicals selected from the group consisting of $C_1$-$C_{12}$alkyl, $C_3$-$C_{12}$-cycloalkyl, phenyl, halogen and $C_1$-$C_{12}$ alkoxy;
$R_3$ is F, Cl, OH, $OR_5$, SH, $SR_5$, $NH_2$, $NHR_5$, $NR_5R_6$ or $R_1R_2C=N-O-$;
wherein $R_1$ and $R_2$ in all groups $R_1R_2C=N-O-$ in the compound of the formula I are identical or different;
if n is 1, $R_4$ is F, Cl, OH, $OR_5$, SH, $SR_5$, $NH_2$, $NHR_5$, $NR_5R_6$ or $R_1R_2C=N-O-$;
wherein $R_1$ and $R_2$ in all groups $R_1R_2C=N-O-$ in the compound of the formula I are identical or different;
if n is 2, $R_4$ is a difunctional group derived from a diol, diamine, aminoalcohol or mercaptoalcohol;
$R_5$ and $R_6$ independently of each other are $C_1$-$C_{18}$alkyl, $C_3$-$C_{12}$cycloalkyl, $C_6$-$C_{14}$aryl or $C_2$-$C_{14}$heteroaryl.
2. A composition according to claim 1, wherein the compound of the formula I, $R_1$ and $R_2$ independently of each other are hydrogen, $NH_2$, $COR_5$, $C_1$-$C_{12}$alkyl or phenyl, or $R_1$ and $R_2$ together with the C atom to which they are linked form a 6 or 12 membered saturated carbocyclic ring or a 5 membered saturated heterocyclic ring which is substituted by one or more radicals selected from the group consisting of $C_1$-$C_{12}$alkyl and $C_3$-$C_{12}$-cycloalkyl;
$R_3$ and $R_4$ are $R_1R_2C=N-O-$;
wherein $R_1$ and $R_2$ in all groups $R_1R_2C=N-O-$ in the compound of the formula I are identical or different; and
$R_5$ is $C_1$-$C_{12}$alkyl.
3. A composition according to claim 1, wherein the amount of functional groups $R_1R_2C=N-O-$ in the compound of formula I in component (b) is from 0.01 to 30 per 100 ethylenically unsaturated functional groups C=C of the polymerizable monomer or oligomer (a).
4. A composition according to claim 2, wherein the amount of functional groups $R_1R_2C=N-O-$ in the compound of formula I in component (b) is from 0.05 to 10 per 100 ethylenically unsaturated functional groups C=C of the polymerizable monomer or oligomer (a).
5. A composition according to claim 1, wherein the amount of functional groups $R_1R_2C=N-O-$ in the compound of formula I in component (b) is from 0.1 to 5.0 per 100 ethylenically unsaturated functional groups C=C of the polymerizable monomer or oligomer (a).
6. A process to generate radicals which comprises reacting the iminoxytriazine compound of the formula I as defined in claim 1 in a reaction triggered by the presence of radicals.
7. A process for preparing polymeric matter, which comprises radical polymerization of the iminoxytriazine compound of the formula I as defined in claim 1.
8. A process for preparing oligomeric, cooligomeric, polymeric or copolymeric matter which comprises subjecting the composition according to claim 1 to convection heat, or to UV-IR-, NIR-, microwave, radiation, ultrasound or to both heat and radiation.
9. The process according to claim 8, wherein the oligomeric, cooligomeric, polymeric or copolymeric matter is in the form of a coating.
10. A process for the controlled degradation of a polyolefin which comprises utilizing the iminoxytriazine compound of the formula I according to claim 1 to lower the molecular weight of said polyolefin and said iminoxytriazine compound of the formula I is incorporated into the polyolefin in a concentration of from 0.001 to 5.0% by weight.
11. The process according to claim 8, wherein the polyolefin is polypropylene, a propylene copolymer or a polypropylene blend.

* * * * *